(12) United States Patent
Moinet et al.

(10) Patent No.: US 7,470,708 B2
(45) Date of Patent: Dec. 30, 2008

(54) ACIDIC QUINOLINE DERIVATIVES AND THEIR USE FOR THE PREVENTION AND/OR TREATMENT OF HYPERGLYCAEMIA-RELATED PATHOLOGIES

(75) Inventors: Gérard Moinet, Orsay (FR); Jean-Claude Correc, Saint-Germain-en-Laye (FR); Annick Arbellot De Vacueur, Fontenay les Briis (FR)

(73) Assignee: Merck Patent Gesellschaft mit Beschraenkter Haftung, Darmstadt (DE)

( * ) Notice: Subject to any disclaimer, the term of this patent is extended or adjusted under 35 U.S.C. 154(b) by 131 days.

(21) Appl. No.: 10/584,151

(22) PCT Filed: Dec. 1, 2004

(86) PCT No.: PCT/EP2004/013662

§ 371 (c)(1),
(2), (4) Date: Jun. 22, 2006

(87) PCT Pub. No.: WO2005/063244

PCT Pub. Date: Jul. 14, 2005

(65) Prior Publication Data

US 2007/0149566 A1 Jun. 28, 2007

(30) Foreign Application Priority Data

Dec. 24, 2003 (FR) .................................. 03 15402

(51) Int. Cl.
*A61K 31/47* (2006.01)
*C07D 215/16* (2006.01)

(52) U.S. Cl. ...................... 514/312; 546/153

(58) Field of Classification Search ................ 514/312; 546/153
See application file for complete search history.

(56) References Cited

U.S. PATENT DOCUMENTS

| 5,026,700 | A | 6/1991 | Harrison et al. |
| 5,245,046 | A | 9/1993 | Youngdale et al. |
| 5,942,540 | A | 8/1999 | Kozachuk |
| 6,025,369 | A | 2/2000 | Rosenquist et al. |
| 2003/0087926 | A1 | 5/2003 | Bloms-Funke et al. |

FOREIGN PATENT DOCUMENTS

| EP | 0 398 283 | 11/1990 |
| EP | 0 433 679 | 6/1991 |
| WO | WO 03/010146 | 2/2003 |
| WO | WO 2004/007461 | 1/2004 |
| WO | WO 2004/045614 | 6/2004 |

OTHER PUBLICATIONS

Harrison, Boyd L. et al: "4'-(Carboxymethyl) Oxy!-and 4'-(Carboxymethyl) Amino!-5,7-Dichloroquino Line-2-Carboxylic Acid: New Antagonists of the Strychnine-Insensitive Glycine Binding Site on the N-Methyl-D-Aspartate (NMDA) Receptor Complex" Journal of Medicinal Chemistry, 33(12), 3130-2 Coden: JMCMAR; ISSN: 0022-2623, 1990, XP001199578.

Salituro, Francesco G. et al: "3-(2-Carboxyindol-3-YL)Propionic Acid-Based Antagonists of the NMDA (N-Methyl-D-Aspartic Acid) Receptor Associated Glycine Binding Site" Journal of Medicinal Chemistry, 35(10), 1791-9 Coden: JMCMAR; ISSN: 0022-2623, 1992, XP001199577.

Database Chemabs 'Online! Chemical Abstracts Service, Columbus, Ohio, US; Kotake, Yahito et al: "Xanthurenic Acid. XVI. Inhibitory Action of 4-Hydroxy-8-Methoxyquinoline-2-Carboxylic Acid, Ethereal Sulfate of Xanthurenic Acid, and Kynurenic Acid on the Diabetogenic Property of Xanthurenic Acid" XP002294269, Retrieved From STN, Database Accession No. 1958:31214 Abstract & Journal of Biochemistry (Tokyo, Japan), 44, 787-95 Coden: Jobiao; ISSN: 0021-924X, 1957.

Carvalho et al."Role of Endogenous Angiotensin II on Glutamatergic Actions in the Rostral Ventrolateral Medulla in Goldblatt Hypertensive Rats" Hypertension, (Oct. 2003) Journal Code: 7906255. ISSN: 1524-4563; XP008034587.

Kotake et al: "A Possible Diabetogenic Role for Tryptophan Metabolites and Effects of Xanthurenic Acid on Insulin" American Journal of Clinical Nutrition, vol. 24, No. 7, Jul. 1971, pp. 826-829, XP000867441; ISSN: 0002-9165.

Sanders et al: L-Amino Acid Inhibition of Epinephrine-Induced Hyperglycemia: Pharmacology, 6(3), 155-63 Coden: ISSN: 0031-7012, 1971, XP008034538.

Stone et al: "Endogenous Kynurenines as Targets for Drug Discovery and Development" Nature Reviews, Drug Discovery, Aug. 2002, vol. 1, No. 8, pp. 609-620, XP008034547; ISSN: 1474-1776.

Edmont et al: "Synthesis and Evaluation of Quinoline Carboxyguanidines as Antidiabetic Agents" Bioorganic & Medicinal Chemistry Letters, 1831-1834 Coden: BMCLE8, ISSN: 0960-894X, 2000, XP002294268.

Nicolaus: "Symbiotic Approach to Drug Design" Decision Makin in Drug Research, 1983, pp. 173-186, XP002197412.

*Primary Examiner*—Taofiq A Solola
(74) *Attorney, Agent, or Firm*—Millen, White, Zelano & Branigan, P.C.

(57) ABSTRACT

The invention relates to compounds of the general formula (I):

in which R1, R2, X, ----- and A are as defined in claim 1.

These compounds can be used in the treatment of hyperglycaemia-related pathologies.

20 Claims, No Drawings

ACIDIC QUINOLINE DERIVATIVES AND THEIR USE FOR THE PREVENTION AND/OR TREATMENT OF HYPERGLYCAEMIA-RELATED PATHOLOGIES

The present invention relates to the use of quinoline derivatives in the treatment of pathologies associated with hyperglycaemia and/or insulin resistance syndrome, in particular non-insulin-dependent diabetes or type II diabetes.

Kynurenines represent the main pathway of tryptophan metabolism. T. W. Stone et al. have put forward the hypothesis of the possible roles of kynurenines in diabetes (T. W. Stone et al., Nature Reviews, vol. 1, August 2002, pp. 609-620), without, however, suggesting the use of quinoline derivatives as antidiabetic agents.

Moreover, D. Edmont et al. have described the antidiabetic effect of 2-carboxy-guanidine derivatives of quinoline (D. Edmont et al, Bioorganic & Medicinal Chemistry Letters, vol. 10, 16, 2000, 1831-1834). However, the antidiabetic effect of quinoline derivatives not containing a carboxyguanidine group is not suggested.

The present invention relates to the use of derivatives of the general formula (I) below for manufacturing a medicament for the prevention of and/or treating hyperglycaemia-related pathologies:

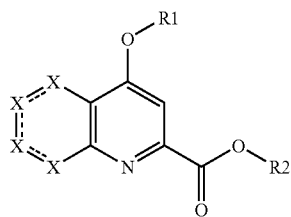

(I)

in which:

X represents, independently of each other, a carbon atom, or a nitrogen, oxygen or sulfur atom; if X represents a carbon atom, it may be optionally substituted by a group chosen from: alkyl, alkenyl, alkynyl, cycloalkyl, heterocycloalkyl, aryl, alkylaryl, heteroaryl, —CN, halogen, —O-aryl, —O-heteroaryl, cycloalkyl, heterocyclyl, —CO$_2$H, —C(=O)-alkyl, —C(=O)-aryl, —C(=O)-cycloalkyl, —C(=O)O-alkyl, —C(=O)NRR', —OH, —O-alkyl, —O-alkylaryl, —C(=O)O-aryl, —NRR', —S(O)$_p$R, in which p represents 0, 1 or 2; or two adjacent carbon atoms may form an aromatic ring fused to the aryl nucleus.

R1 and R2, which may be identical or different, independently represent a group chosen from:

Hydrogen, alkyl, alkenyl, alkynyl, each optionally and independently substituted by one or more of the following groups:
—CN, halogen, aryl, biaryl, —O-aryl, —O-heteroaryl, —O-heterocycloalkyl, cycloalkyl, heterocycloalkyl, —CO$_2$H, —C(=O)-alkyl, —C(=O)-aryl, —C(=O)-cycloalkyl, —C(=O)O-alkyl, —C(=O)NRR', —OH, —O-alkyl, —O-alkylaryl, —C(=O)O-aryl, —NRR', —S(O)$_p$R, in which p represents 0, 1 or 2; in which:

aryl is optionally and independently substituted by one or more groups chosen from: —CN, halogen, aryl, alkyl, —O-alkyl, -alkyl-C(=O)O-alkyl, -alkyl-C(=O)OH, —O-alkylaryl, heterocycloalkyl, —NRR', —OH, —S(O)$_p$R, in which p represents 0, 1 or 2; —O-aryl, perhaloalkyl, —COOH, COOR;

heteroaryl is optionally and independently substituted by one or more groups chosen from halogen, —COOH, COOR and heterocycloalkyl;

heterocycloalkyl is optionally and independently substituted by one or more alkyl or =O;

cycloalkyl or heterocycloalkyl, each optionally and independently substituted by alkyl or alkoxy;

aryl or heteroaryl, each optionally and independently substituted by one or more groups chosen from —CN, halogen, aryl, alkyl, —O-alkyl, -alkyl-C(=O)O-alkyl, —O-alkylaryl, heterocycloalkyl; —NRR', —OH, —S(O)$_p$R, in which p represents 0, 1 or 2; —O-aryl, perhaloalkyl, —COOH, COOR;

R and R' are chosen from H and alkyl;

- - - - represents a single bond or a double bond and also the tautomeric forms, enantiomers, diastereoisomers and epimers, and the pharmaceutically acceptable salts.

Preferably, each of the X represents a carbon atom; preferably, each of the X represents a carbon atom optionally substituted by a halogen atom; preferably, the carbon in position 6 of the quinoline ring is substituted by a halogen atom, preferably fluorine;

If R1 and/or R2 represent(s) alkyl, alkenyl or alkynyl, they are preferably optionally substituted by —CN, halogen, —O-aryl, —O-heteroaryl, cycloalkyl, heterocycloalkyl, —COOH, —C(=O)-aryl, —C(=O)-cycloalkyl, —C(=O)O-alkyl, —C(=O)NRR', biaryl or aryl, in which aryl is optionally substituted by —CN, halogen, aryl, alkyl, —O-alkyl, -alkyl-C(=O)O-alkyl, alkylCOOH, —O-alkylaryl or heterocycloalkyl.

Preferably, R1 represents alkyl, alkenyl, alkynyl, cycloalkyl, heterocycloalkyl, alkylaryl, aryl or heteroaryl, which are optionally substituted, as defined hereinabove or hereinbelow.

Preferably, R1 represents alkyl or alkenyl, which are optionally substituted, as defined hereinabove or hereinbelow.

Preferably, R1 represents alkyl or alkenyl, preferably alkyl, optionally and independently substituted by one or more groups chosen from: —CN, aryl, hetero-cycloalkyl, biaryl, halogen, —C(=O)-aryl, —O-aryl, —C(=O)-alkyl, cycloalkyl, —C(=O)-alkyl, —COOH, —O-heteroaryl, —C(=O)NRR', —C(=O)-cycloalkyl, —O-heterocycloalkyl;

in which aryl is optionally and independently substituted by one or more halogen, —CN, —O-alkylaryl, aryl, alkyl, —O-alkyl, heterocycloalkyl, -alkyl-C(=O)—OH, -alkyl-C(=O)O-alkyl;

heteroaryl is optionally substituted by heterocycloalkyl, halogen or —COOH.

heterocycloalkyl is optionally and independently substituted by one or more groups chosen from =O and alkyl.

Preferably, R1 represents alkyl or alkenyl in which the carbon α to the oxygen atom is substituted by —COOH, —C(=O)-alkyl, —C(=O)-aryl, —C(=O)-cycloalkyl, —C(=O)O-alkyl or —C(=O)NRR', in which alkyl and aryl are optionally substituted as defined hereinabove or hereinbelow, and RR' are as defined hereinabove or hereinbelow.

Preferably, R1 represents alkyl or alkenyl, each optionally substituted by halogen, —O-heteroaryl or —C(=O)-aryl, in which aryl is optionally substituted by one or more —O-alkyl and heteroaryl is optionally substituted by one or more —COOH or halogen.

Preferably, R2 represents a hydrogen atom or an alkyl group, preferably methyl.

Preferably, R and R' represent a hydrogen atom or a methyl or ethyl radical.

Preferably, the compounds of the formula (I) are represented by the general formula (II) below:

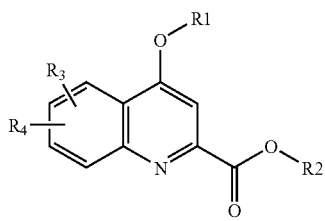

(II)

in which R1 and R2 are as defined above and

R3 and R4, which may be identical or different, independently represent groups chosen from alkyl, alkenyl, alkynyl, cycloalkyl, heterocycloalkyl, aryl, alkylaryl, heteroaryl, —CN, halogen, —O-aryl, —O-heteroaryl, cycloalkyl, heterocyclyl, —CO₂H, —C(=O)-alkyl, —C(=O)-aryl, —C(=O)-cycloalkyl, —C(=O)O-alkyl, —C(=O)NRR', —OH, —O-alkyl, —O-alkylaryl, —C(=O)O-aryl, —NRR' and —S(O)$_p$R, in which p represents 0, 1 or 2, or R3 and R4 may together also form a heterocycle adjacent to the phenyl ring, and also the tautomeric forms, enantiomers, diastereoisomers and epimers, and the pharmaceutically acceptable salts.

Preferably, R3 and R4 represent H, —O-alkyl and/or a halogen atom, preferably halogen in position 6; preferably, R3 and/or R4 represent(s) fluorine or H.

If R3 and R4 together form a heterocycle adjacent to the phenyl ring, they may especially represent the ring —O—(CH₂)$_n$—O—, n being an integer ranging from 1 to 4.

The compounds of the formula (I) in which:

X and R2 are defined as above and

R1 represents alkyl in which the carbon a to the oxygen atom is substituted by —COOH, —C(=O)-alkyl, —C(=O)-aryl, —C(=O)-cycloalkyl, —C(=O)O-alkyl or —C(=O)NRR', in which alkyl and aryl are optionally substituted as defined hereinabove or hereinbelow, and RR' are as defined hereinabove or hereinbelow, are of most particular interest and as such form part of the present invention.

They are represented by the general formula (III) below:

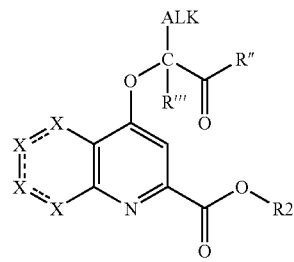

(III)

in which

X, R2, R, R' and ⋯⋯ are as defined above;

ALK represents an alkyl or alkenyl radical optionally substituted by one or more of the following groups: —CN, halogen, aryl, biaryl, —O-aryl, —O-heteroaryl, —O-heterocycloalkyl, cycloalkyl, heterocycloalkyl, —CO₂H, —C(=O)-alkyl, —C(=O)-aryl, —C(=O)-cycloalkyl, —C(=O)O-alkyl, —C(=O)NRR', —OH, —O-alkyl, —O-alkylaryl, —C(=O)O-aryl, —NRR', —S(O)$_p$R, in which p represents 0, 1 or 2;

R ' ' is chosen from —OH, alkyl, aryl, cycloalkyl, —O-alkyl and —NRR', in which:

alkyl is optionally substituted by one or more of the following groups: —CN, halogen, aryl, biaryl, —O-aryl, —O-heteroaryl, —O-heterocycloalkyl, cycloalkyl, heterocycloalkyl, —CO₂H, —C(=O)-alkyl, —C(=O)-aryl, —C(=O)-cycloalkyl, —C(=O)O-alkyl, —C(=O)NRR', —OH, —O-alkyl, —O-alkylaryl, —C(=O)O-aryl, —NRR', —S(O)$_p$R, in which p represents 0, 1 or 2; and aryl is optionally substituted by one or more groups chosen from: —CN, halogen, aryl, alkyl, —O-alkyl, -alkyl-C(=O)O-alkyl, -alkyl-C(=O)OH, —O-alkylaryl, heterocycloalkyl, —NRR', —OH, —S(O)$_p$R, in which p represents 0, 1 or 2, —O-aryl, perhaloalkyl, —COOH, COOR;

heteroaryl is optionally and independently substituted by one or more groups chosen from halogen, —COOH and heterocycloalkyl;

heterocycloalkyl is optionally and independently substituted by one or more alkyl or =O;

R''' is H, alkyl or alkenyl optionally substituted by one or more of the following groups: —CN, halogen, aryl, biaryl, —O-aryl, —O-heteroaryl, —O-heterocycloalkyl, cycloalkyl, heterocycloalkyl, —CO₂H, —C(=O)-alkyl, —C(=O)-aryl, —C(=O)-cycloalkyl, —C(=O)O-alkyl, —C(=O)NRR', —OH, —O-alkyl, —O-alkylaryl, —C(=O)O-aryl, —NRR', —S(O)$_p$R, in which p represents 0, 1 or 2;

and also the tautomeric forms, enantiomers, diastereoisomers and epimers, and the pharmaceutically acceptable salts.

In the general formula (III), preferably, X and R2 are as defined above, R ' ' represents —OH, alkyl, aryl, cycloalkyl, —O-alkyl or —NRR', in which aryl is optionally substituted by —O-alkylaryl, —O-alkyl, alkyl, aryl or halogen;

ALK represents alkyl optionally substituted by aryl;

R''' represents H;

X each represent a carbon atom, optionally substituted by a halogen atom, preferably fluorine; even more preferably in position 6 of the quinoline ring system;

R2 represents H or an alkyl radical, preferably methyl.

The compounds of the formula (I) may especially be chosen from:

methyl 4-(1,3-benzothiazol-2-ylmethoxy)-6-fluoroquinoline-2-carboxylate
methyl 4-[(4-bromo-2-fluorobenzyl)oxy]-6-fluoroquinoline-2-carboxylate
methyl 4-ethoxy-6-fluoroquinoline-2-carboxylate
methyl 4-[(4-bromo-2-fluorobenzyl)oxy]-6-methoxyquinoline-2-carboxylate
methyl 6-fluoro-4-[(3-methylbut-2-en-1-yl)oxy]quinoline-2-carboxylate
methyl 4-[(2'-cyanobiphenyl-4-yl)methoxy]-6-fluoroquinoline-2-carboxylate
methyl 4-(cyanomethoxy)-6-fluoroquinoline-2-carboxylate
methyl 4-(2-chloroethoxy)-6-fluoroquinoline-2-carboxylate
methyl 4-(2-amino-2-oxoethoxy)-6-fluoroquinoline-2-carboxylate
methyl 4-(allyloxy)-6-fluoroquinoline-2-carboxylate
methyl 6-fluoro-4-(pentyloxy)quinoline-2-carboxylate
methyl 4-[2-(4-chlorophenyl)-2-oxoethoxy]-6-fluoroquinoline-2-carboxylate
methyl 6-fluoro-4-(2-oxo-2-phenylethoxy)quinoline-2-carboxylate
methyl 6-fluoro-4-[2-(4-fluorophenoxy)ethoxy]quinoline-2-carboxylate
methyl 6-fluoro-4-(2-phenylethoxy)quinoline-2-carboxylate
methyl 6-fluoro-4-(2-phenoxyethoxy)quinoline-2-carboxylate
methyl 6-fluoro-4-(3-phenylpropoxy)quinoline-2-carboxylate
methyl 4-(2-biphenyl-4-yl-2-oxoethoxy)-6-fluoroquinoline-2-carboxylate
methyl 6-fluoro-4-[2-(4-methylphenyl)-2-oxoethoxy]quinoline-2-carboxylate
methyl 6-fluoro-4-[2-(4-methoxyphenyl)-2-oxoethoxy]quinoline-2-carboxylate
methyl 4-[2-(1-adamantyl)-2-oxoethoxy]-6-fluoroquinoline-2-carboxylate
methyl 6-fluoro-4-[2-(4-fluorophenyl)-2-oxoethoxy]quinoline-2-carboxylate
methyl 4-[2-(3,4-dichlorophenyl)-2-oxoethoxy]-6-fluoroquinoline-2-carboxylate
methyl 6-fluoro-4-[2-(3-methoxyphenyl)-2-oxoethoxy]quinoline-2-carboxylate
methyl 4-[4-(4-chlorophenoxy)butoxy]-6-fluoroquinoline-2-carboxylate
methyl 6-fluoro-4-[2-(3-fluorophenoxy)ethoxy]quinoline-2-carboxylate
methyl 4-[2-(4-bromophenoxy)ethoxy]-6-fluoroquinoline-2-carboxylate
methyl 6-fluoro-4-{[5-(4-fluorophenoxy)pentyl]oxy}quinoline-2-carboxylate
methyl 4-[2-(4-cyanophenoxy)ethoxy]-6-fluoroquinoline-2-carboxylate
methyl 6-fluoro-4-{2-[(4-morpholin-4-yl-1,2,5-thiadiazol-3-yl)oxy]ethoxy}quinoline-2-carboxylate
methyl 6-fluoro-4-{2-[4-(3-methoxy-3-oxopropyl)phenoxy]ethoxy}quinoline-2-car-boxylate
methyl 6-fluoro-4-[2-(1-naphthyloxy)ethoxy]quinoline-2-carboxylate
methyl 6-fluoro-4-[2-(2-methoxyphenoxy)ethoxy]quinoline-2-carboxylate
methyl 4-{2-[2-(benzyloxy)phenyl]-2-oxoethoxy}-6-fluoroquinoline-2-carboxylate
methyl 6-fluoro-4-[2-(2-naphthyloxy)ethoxy]quinoline-2-carboxylate
methyl 4-[2-(1,3-dioxo-1,3-dihydro-2H-isoindol-2-yl)ethoxy]-6-fluoroquinoline-2-carboxylate
methyl 4-[1-(ethoxycarbonyl)-3-phenylpropoxy]-6-fluoroquinoline-2-carboxylate
methyl 4-[2-(2,3-dimethylphenoxy)ethoxy]-6-fluoroquinoline-2-carboxylate
methyl 6-fluoro-4-{2-[4-(2-methyl-1,3-dioxolan-2-yl)phenyl]ethoxy}quinoline-2-carboxylate
methyl 4-{2-[4-(benzyloxy)phenyl]-2-oxoethoxy}-6-fluoroquinoline-2-carboxylate
methyl 4-[2-(3,4-dimethoxyphenyl)-2-oxoethoxy]-6-fluoroquinoline-2-carboxylate
methyl 4-(3-chloropropoxy)-6-fluoroquinoline-2-carboxylate
methyl 4-(3-chloro-2-methylpropoxy)-6-fluoroquinoline-2-carboxylate
methyl 4-(1-ethylpropoxy)-6-fluoroquinoline-2-carboxylate
methyl 6-fluoro-4-[(1-methylhexyl)oxy]quinoline-2-carboxylate
methyl 4-[2-(2,4-dimethoxyphenyl)-2-oxoethoxy]-6-fluoroquinoline-2-carboxylate
methyl 4-(3,3-dimethyl-2-oxobutoxy)-6-fluoroquinoline-2-carboxylate
methyl 6-fluoro-4-(3-phenoxypropoxy)quinoline-2-carboxylate
4-[(4-bromo-2-fluorobenzyl)oxy]-6-fluoroquinoline-2-carboxylic acid
4-(1,3-benzothiazol-2-ylmethoxy)-6-fluoroquinoline-2-carboxylic acid
4-ethoxy-6-fluoroquinoline-2-carboxylic acid
4,4'-[(2E)-but-2-ene-1,4-diylbis(oxy)]bis(6-fluoroquinoline-2-carboxylic acid)
6-fluoro-4-[(3-methylbut-2-en-1-yl)oxy]quinoline-2-carboxylic acid
4-[(2'-cyanobiphenyl-4-yl)methoxy]-6-fluoroquinoline-2-carboxylic acid
sodium 4-[(4-bromo-2-fluorobenzyl)oxy]-6-methoxyquinoline-2-carboxylate
4-(cyanomethoxy)-6-fluoroquinoline-2-carboxylic acid
4-(2-chloroethoxy)-6-fluoroquinoline-2-carboxylic acid
4-(2-amino-2-oxoethoxy)-6-fluoroquinoline-2-carboxylic acid
4-(allyloxy)-6-fluoroquinoline-2-carboxylic acid
4-(3-chloropropoxy)-6-fluoroquinoline-2-carboxylic acid
4-(3-chloro-2-methylpropoxy)-6-fluoroquinoline-2-carboxylic acid
6-fluoro-4-(pentyloxy)quinoline-2-carboxylic acid
4-(cyclohexylmethoxy)-6-fluoroquinoline-2-carboxylic acid
6-fluoro-4-[2-(4-fluorophenoxy)ethoxy]quinoline-2-carboxylic acid
6-fluoro-4-(2-phenylethoxy)quinoline-2-carboxylic acid
6-fluoro-4-(3-phenylpropoxy)quinoline-2-carboxylic acid
4-[2-(1-adamantyl)-2-oxoethoxy]-6-fluoroquinoline-2-carboxylic acid
6-fluoro-4-[2-(4-fluorophenyl)-2-oxoethoxy]quinoline-2-carboxylic acid
6-fluoro-4-[2-(3-methoxyphenyl)-2-oxoethoxy]quinoline-2-carboxylic acid
4-[4-(4-chlorophenoxy)butoxy]-6-fluoroquinoline-2-carboxylic acid
6-fluoro-4-[2-(3-fluorophenoxy)ethoxy]quinoline-2-carboxylic acid
4-[2-(4-bromophenoxy)ethoxy]-6-fluoroquinoline-2-carboxylic acid
6-fluoro-4-{[5-(4-fluorophenoxy)pentyl]oxy}quinoline-2-carboxylic acid 4-[2-(4-cyanophenoxy)ethoxy]-6-fluoroquinoline-2-carboxylic acid
6-fluoro-4-{2-[(4-morpholin-4-yl-1,2,5-thiadiazol-3-yl)oxy]ethoxy}quinoline-2-car-boxylic acid
4-{2-[4-(2-carboxyethyl)phenoxy]ethoxy}-6-fluoroquinoline-2-carboxylic acid
6-fluoro-4-[2-(2-methoxyphenoxy)ethoxy]quinoline-2-carboxylic acid
4-(1-carboxy-3-phenylpropoxy)-6-fluoroquinoline-2-carboxylic acid
4-[2-(2,3-dimethylphenoxy)ethoxy]-6-fluoroquinoline-2-carboxylic acid
4-[2-(3,4-dimethoxyphenyl)-2-oxoethoxy]-6-fluoroquinoline-2-carboxylic acid and also the tautomeric forms, enantiomers, diastereoisomers and epimers, and the pharmaceutically acceptable salts.

More preferably, the compounds of the formula (I) may be chosen from:
-4-(4-bromo-2-fluorobenzyloxy)-6-fluoroquinoline-2-carboxylic acid
4-(benzothiazol-2-ylmethoxy)-6-fluoroquinoline-2-carboxylic acid
4-ethoxy-6-fluoroquinoline-2-carboxylic acid
4-(4-bromo-2-fluorobenzyloxy)-6-methoxyquinoline-2-carboxylic acid (sodium salt)
4-({(E)-4-[(2-carboxy-6-fluoro-4-quinolinyl)oxy]-2-butenyl}oxy)-6-fluoro-quinoline-2-carboxylic acid
6-fluoro-4-(3-methylbut-2-enyloxy)quinoline-2-carboxylic acid
4-(2'-cyanobiphenyl-4-ylmethoxy)-6-fluoroquinoline-2-carboxylic acid
4-[2-(3,4-dimethoxyphenyl)-2-oxo-ethoxy]-6-fluoroquinoline-2-carboxylic acid
methyl 4-(3-chloro-propoxy)-6-fluoroquinoline-2-carboxylate
methyl 4-(3-chloro-2-methylpropoxy)-6-fluoroquinoline-2-carboxylate and also the tautomeric forms, enantiomers, diastereoisomers and epimers, and the pharmaceutically acceptable salts.

According to the present invention, the alkyl radicals represent saturated hydrocarbon-based radicals in a straight or branched chain of 1 to 20 carbon atoms and preferably of 1 to 5 carbon atoms.

If they are linear, mention may be made especially of methyl, ethyl, propyl, butyl, pentyl, hexyl, octyl, nonyl, decyl, dodecyl, hexadecyl and octadecyl radicals.

If they are branched or substituted by one or more alkyl radicals, mention may be made especially of isopropyl, tert-butyl, 2-ethylhexyl, 2-methylbutyl, 2-methylpentyl, 1-methylpentyl and 3-methylheptyl radicals.

The alkoxy radicals according to the present invention are radicals of the formula —O-alkyl, the alkyl being as defined above.

Among the halogen atoms, mention is made more particularly of fluorine, chlorine, bromine and iodine atoms, preferably fluorine.

The alkenyl radicals represent hydrocarbon-based radicals in a straight or linear chain, and comprise one or more ethylenic unsaturations. Among the alkenyl radicals that may especially be mentioned are allyl or vinyl radicals.

The alkynyl radicals represent hydrocarbon-based radicals in a straight or linear chain, and comprise one or more acetylenic unsaturations. Among the alkynyl radicals, mention may be made especially of acetylene.

The cycloalkyl radical is a mono-, bi- or tricyclic, saturated or partially unsaturated, non-aromatic hydrocarbon-based radical of 3 to 10 carbon atoms, such as, especially, cyclopropyl, cyclopentyl, cyclohexyl or adamantyl, and also the corresponding rings containing one or more unsaturations.

Aryl denotes a mono- or bicyclic hydrocarbon-based aromatic system of 6 to 10 carbon atoms.

Among the alkyl radicals that may especially be mentioned are the phenyl or naphthyl radical, more particularly substituted by at least one halogen atom.

Among the alkylaryl radicals that may especially be mentioned are the benzyl or phenethyl radical.

The heteroaryl radicals denote mono- or bicyclic aromatic systems of 5 to 10 carbon atoms, comprising one or more hetero atoms chosen from nitrogen, oxygen and sulfur. Among the heteroaryl radicals that may be mentioned are pyrazinyl, thienyl, oxazolyl, furazanyl, pyrrolyl, 1,2,4-thiadiazolyl, naphthyridinyl, pyridazinyl, quinoxalinyl, phthalazinyl, imidazo[1,2-a]pyridyl, imidazo[2,1-b]thiazolyl, cinnolinyl, triazinyl, benzofurazanyl, azaindolyl, benzimidazolyl, benzothienyl, thienopyridyl, thienopyrimidinyl, pyrrolopyridyl, imidazopyridyl, benzazaindolyl, 1,2,4-triazinyl, benzothiazolyl, furanyl, imidazolyl, indolyl, triazolyl, tetrazolyl, indolizinyl, isoxazolyl, isoquinolyl, isothiazolyl, oxadiazolyl, pyrazinyl, pyridazinyl, pyrazolyl, pyridyl, pyrimidinyl, purinyl, quinazolinyl, quinolyl, isoquinolyl, 1,3,4-thiadiazolyl, thiazolyl, triazinyl, isothiazolyl and carbazolyl, and also the corresponding groups derived from their fusion or from fusion with the phenyl nucleus. The preferred heteroaryl groups comprise thienyl, pyrrolyl, quinoxalinyl, furanyl, imidazolyl, indolyl, isoxazolyl, isothiazolyl, pyrazinyl, pyridazinyl, pyrazolyl, pyridyl, pyrimidinyl, quinazolinyl, quinolyl, thiazolyl, carbazolyl and thiadiazolyl, and groups derived from fusion with a phenyl nucleus, and more particularly quinolyl, carbazolyl and thiadiazolyl.

The heterocycloalkyl radicals denote mono- or bicyclic, saturated or partially unsaturated, non-aromatic systems of 5 to 10 carbon atoms, comprising one or more hetero atoms chosen from N, O and S. Among the heterocycloalkyls that may especially be mentioned are epoxyethyl, oxiranyl, aziridinyl, tetrahydrofuranyl, dioxolanyl, pyrrolidinyl, pyrazolidinyl, imidazolidinyl, tetrahydrothiophenyl, dithiolanyl, thiazolidinyl, tetrahydropyranyl, dioxanyl, morpholinyl, piperidyl, piperazinyl, tetrahydrothiopyranyl, dithianyl, thiomorpholinyl, dihydrofuranyl, 2-imidazolinyl, 2,3-pyrrolinyl, pyrazolinyl, dihydrothiophenyl, dihydropyranyl, pyranyl, tetrahydropyridyl, dihydropyridyl, tetrahydropyrimidinyl and dihydrothiopyranyl, and the corresponding groups derived from fusion with a phenyl nucleus, and more particularly morpholinyl, dioxalanyl, benzothiazolidinyl, pyrrolidinyl and benzopyrrolidinyl rings.

The expression "pharmaceutically acceptable salts" refers to the relatively non-toxic mineral and organic acid-addition salts, and the base-addition salts, of the compounds of the present invention. These salts can be prepared in situ during the final isolation and purification of the compounds. In particular, the acid-addition salts can be prepared by separately reacting the purified compound in its purified form with an organic or mineral acid and isolating the salt thus formed. Among the examples of acid-addition salts are the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, sulfamates, malonates, salicylates, propionates, methylenebis-b-hydroxy-naphthoates, gentisic acid, isethionates, di-p-toluoyltartrates, methanesulfonates, ethanesulfonates, benzenesulfonates, p-toluenesulfonates, cyclohexyl sulfamates and quinates-laurylsulfonate, and analogues. (See for example S. M. Berge et al. "Pharmaceutical Salts" *J. Pharm. Sci*, 66: pp. 1-19 (1977) which is incorporated herein by reference). The acid-addition salts can also be prepared by separately reacting the purified compound in its acid form with an organic or mineral base and isolating the salt thus formed. The acid-addition salts include amine salts and metal salts. The suitable metal salts include the sodium, potassium, calcium, barium, zinc, magnesium and aluminium salts. The sodium and potassium salts are preferred. The suitable mineral base-addition salts are prepared from metallic bases including sodium hydride, sodium hydroxide, potassium hydroxide, calcium hydroxide, aluminium hydroxide, lithium hydroxide, magnesium hydroxide and zinc hydroxide. The suitable amine base-addition salts are prepared from amines whose basicity is sufficient to form a stable salt, and preferably include amines that are often used in medicinal chemistry on account of their low toxicity and their acceptability for medical use: ammonia, ethylenediamine, N-methylglucamine, lysine, arginine, ornithine, choline, N,N'-dibenzylethylenediamine, chloroprocaine, diethanolamine, procaine, N-benzyl-phenethylamine, diethylamine, piperazine, tris(hydroxymethyl)aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, for example lysine and arginine, and dicyclohexylamine, and analogues.

The invention also relates to the tautomeric forms, enantiomers, diastereoisomers, epimers and organic or mineral salts of the compounds of the general formula (I).

The compounds of the invention of the formula (I) as defined above containing a sufficiently acidic function or a sufficiently basic function, or both, can include the corresponding pharmaceutically acceptable salts of an organic or mineral acid or of an organic or mineral base.

The compounds of the general formula (I) can be prepared by application or adaptation of any method known per se and/or within the capacity of a person skilled in the art, especially those described by Larock in *Comprehensive Organic Transformations*, VCH Pub., 1989, or by application or adaptation of the processes described in the examples that follow, or alternatively, more particularly, according to the following method described in *Bioorganic & Medicinal Chemistry Letters* 10(16), 2000, 1831-34:

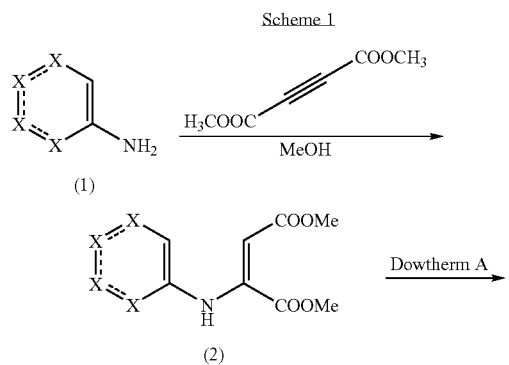

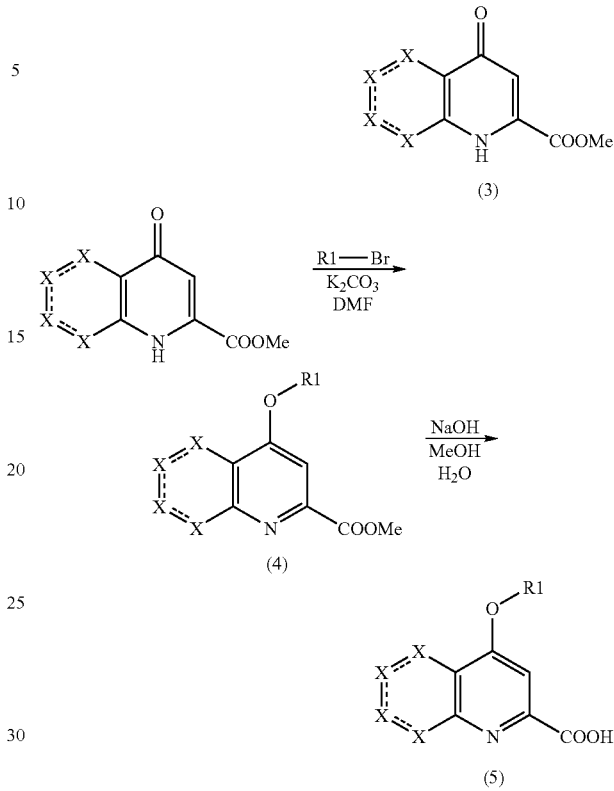

Compound (1) is condensed with the acetylenedicarboxylate by heating in alcoholic medium, preferably in methanol. Compound (2) obtained is cyclized at reflux in a solvent, such as diphenyl ether or Dowtherm A. Compound (3) obtained is O-alkylated in alkaline medium, preferably in DMF in the presence of potassium carbonate at 50° C., and the ester (4) obtained is then saponified, preferably with caustic soda in alcoholic medium.

The compounds of the formula (I) for which R2 is other than H are then obtained by esterification of (4) with the corresponding alcohol R2-OH.

According to another subject, the present invention thus also relates to the process for the preparation of the compounds of the formula (III) described above, comprising the step consisting in reacting a compound of the formula (3)

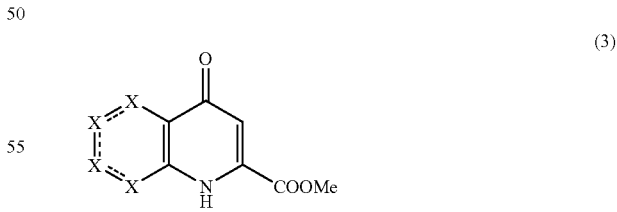

in which X and ----- are as defined above, with a compound of the formula R1-Hal, in which Hal represents a halogen atom, and R1 is as defined above, in a suitable organic solvent, in alkaline medium, at a temperature of between room temperature and the boiling point of the solvent, and optionally, if R2 is other than methyl, the step consisting in saponifying the product obtained, in an alcoholic solvent, in the presence of a base, optionally followed, if R2 is other than H, by the step consisting in esterifying the product obtained with a corresponding alcohol of the formula R2-OH, in which R2 is as defined above, in an alcoholic solvent, in acidic medium.

Optionally, the said process may also include the step consisting in isolating the product obtained.

In the reactions described hereinbelow, it may be necessary to protect reactive functional groups, for example hydroxyl, amino, imino, thio or carboxyl groups, if they are desired in the final product, to avoid their unwanted participation in the reactions. The conventional protecting groups can be used in accordance with the standard practice; for examples, see T. W. Green and P. G. M. Wuts in *Protective Groups in Organic Chemistry*, John Wiley and Sons, 1991; J. F. W. McOmie in *Protective Groups in Organic Chemistry*, Plenum Press, 1973.

The compound thus prepared can be recovered from the reaction mixture via the conventional means. For example, the compounds can be recovered by distilling the solvent from the reaction mixture or, if necessary, after distilling off the solvent from the mixture of the solution, pouring the remainder into water, followed by extraction with a water-immiscible organic solvent, and distilling the solvent from the extract. In addition, the product can also be purified, if so desired, by various techniques, such as recrystallization, reprecipitation or various chromatographic techniques, especially column chromatography or preparative thin-layer chromatography.

It will be appreciated that the compounds that are useful according to the present invention may contain asymmetric centres. These asymmetric centres can be, independently, of R or S configuration. It will be apparent to a person skilled in the art that certain compounds that are useful according to the invention may also exhibit geometrical isomerism. It should be understood that the present invention includes individual geometrical isomers and stereoisomers, and mixtures thereof, including racemic mixtures, of compounds of the formula (I) above. Isomers of this type can be separated from their mixtures by application or adaptation of known processes, for example chromatography techniques or recrystallization techniques, or they are prepared separately from suitable isomers of their intermediates.

For the purposes of the present text, it is understood that the tautomeric forms are included in the citation of a given group, for example thio/mercapto or oxo/hydroxyl.

The acid-addition salts are formed with the compounds that are useful according to the invention in which a basic function, such as an amino, alkylamino or dialkylamino group is present. The pharmaceutically acceptable, i.e. non-toxic, acid-addition salts are preferred. The selected salts are optimally chosen so as to be compatible with the usual pharmaceutical vehicles and suitable for oral or parenteral administration. The acid-addition salts of the compounds that are useful according to the present invention can be prepared by reacting the free base with the appropriate acid, by application or adaptation of known processes. For example, the acid-addition salts of the compounds that are useful according to the present invention can be prepared either by dissolving the free base in water or in a basified aqueous solution or suitable solvents containing the appropriate acid, and isolating the solvent by evaporating the solution, or by reacting the free base and the acid in an organic solvent, in which case the salt separates out directly or can be obtained by concentrating the solution. Among the acids that are suitable for use in the preparation of these salts are hydrochloric acid, hydrobromic acid, phosphoric acid, sulfuric acid, various organic carboxylic and sulfonic acids, such as acetic acid, citric acid, propionic acid, succinic acid, benzoic acid, tartaric acid, fumaric acid, mandelic acid, ascorbic acid, malic acid, methanesulfonic acid, toluenesulfonic acid, fatty acids, adipate, alginate, ascorbate, aspartate, benzenesulfonate, benzoate, cyclopentanepropionate, digluconate, dodecyl sulfate, bisulfate, butyrate, lactate, laurate, lauryl sulfate, malate, hydriodide, 2-hydroxyethanesulfonate, glycerophosphate, picrate, pivalate, pamoate, pectinate, persulfate, 3-phenylpropionate, thiocyanate, 2-naphthalenesulfonate, undecanoate, nicotinate, hemisulfate, heptonate, hexanoate, camphorate, camphorsulfonate and the like.

The acid-addition salts of the compounds that are useful according to the present invention can be regenerated from the salts by application or adaptation of known processes. For example, the parent compounds that are useful according to the invention can be regenerated from their acid-addition salts by treatment with an alkali, for example aqueous sodium bicarbonate solution or aqueous ammonia solution.

The compounds that are useful according to the present invention can be regenerated from their base-addition salts by application or adaptation of known processes. For example, the parent compounds that are useful according to the invention can be regenerated from their base-addition salts by treatment with an acid, for example hydrochloric acid.

The base-addition salts can be formed if the compound that is useful according to the invention contains a carboxyl group, or a sufficiently acidic bioisostere. The bases that can be used to prepare the base-addition salts preferably include those that produce, if they are combined with a free acid, pharmaceutically acceptable salts, i.e. salts whose cations are not toxic to the patient in the pharmaceutical doses of the salts, such that the beneficial inhibitory effects intrinsic to the free base are not negated by the side effects attributable to the cations. The pharmaceutically acceptable salts, including those derived from alkaline-earth metal salts, within the scope of the present invention include those derived from the following bases: sodium hydride, sodium hydroxide, potassium hydroxyide, calcium hydroxide, aluminium hydroxide, lithium hydroxide, magnesium hydroxide, zinc hydroxide, ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) amino-methane, tetramethylammonium hydroxide and the like.

The compounds that are useful according to the present invention can be readily prepared, or formed during the process of the invention, in the form of solvates (for example hydrates). The hydrates of the compounds that are useful according to the present invention can be readily prepared by recrystallization of an aqueous/organic solvent mixture, using organic solvents, such as dioxane, tetrahydrofuran or methanol.

The basic products or the intermediates can be prepared by application or adaptation of known processes, for example processes as described in the Reference Examples or obvious chemical equivalents thereof.

According to the present invention, the compounds of the formula (I) have hypoglycaemiant activity. They can reduce hyperglycaemia, more particularly the hyperglycaemia of non-insulin-dependent diabetes.

Insulin resistance is characterized by a reduction in the action of insulin (cf. Presse Médicale, 1997, 26 (No 14), 671-677) and is involved in a large number of pathological conditions, such as diabetes and more particularly non-insulin-dependent diabetes (type II diabetes or NIDDM), dyslipidaemia, obesity and certain microvascular and macrovascular complications, for instance atherosclerosis, arterial hypertension, inflammatory processes, macroangiopathy, microangiopathy, retinopathy and neuropathy.

In this respect, reference will be made, for example, to Diabetes, vol. 37, 1988, 1595-1607; *Journal of Diabetes and Its Complications,* 1998, 12, 110-119 or Horm. Res., 1992, 38, 28-32.

In particular, the compounds of the invention show strong anti-hyperglycaemic activity.

The compounds of the formula (I) are thus useful in the treatment of hyper-glycaemia-related pathologies.

The present invention also relates to the use of compounds of the general formula (I) for the preparation of pharmaceutical compositions for the prevention of and/or treating hyperglycaemia-related pathologies, more particularly diabetes.

The pharmaceutical compositions according to the invention can be presented in forms intended for parenteral, oral, rectal, permucous or percutaneous administration.

They will thus be presented in the form of injectable solutions or suspensions or multi-dose bottles, in the form of plain or coated tablets, sugar-coated tablets, wafer capsules, gel capsules, pills, cachets, powders, suppositories or rectal capsules, solutions or suspensions, for percutaneous use in a polar solvent, or for permucous use.

The excipients that are suitable for such administrations are cellulose or microcrystalline cellulose derivatives, alkaline-earth metal carbonates, magnesium phosphate, starches, modified starches and lactose for solid forms.

For rectal use, cocoa butter or polyethylene glycol stearates are the preferred excipients.

For parenteral use, water, aqueous solutions, physiological saline and isotonic solutions are the vehicles most appropriately used.

The dosage can vary within wide ranges (0.5 mg to 1000 mg) according to the therapeutic indication and the route of administration, and also to the age and weight of the patient.

The examples that follow illustrate the invention without, however, limiting it. The starting materials used are known products or are prepared according to known procedures.

Unless otherwise mentioned, the percentages are expressed on a weight basis.

EXAMPLE 1

4-Ethoxy-6-fluoroquinoline-2-carboxylic acid 2-(4-Fluorophenylamino)but-2-enedioic acid dimethyl ester 50 ml (0.51 M) of 4-fluoroaniline (at 98%) are introduced into 500 ml of anhydrous methanol, followed by dropwise addition of 70.5 ml (0.56 M) of methyl acetylenedicarboxylate (at 98%). The reaction mixture is heated at 55° C. with stirring for 3 hours, and then evaporated under reduced pressure. The residue is purified by evolution through silica.

113.2 g of yellow oil are obtained.
Yield: 87%
$^1$H NMR (CDCl$_3$):
9.74 (1H, s); 7.06 (4H, m); 5.55 (1H, s); 3.88 (3H, s); 3.84 (3H, s);

Methyl 6-fluoro-4-oxo-1,4-dihydroquinoline-2-carboxylate 250 ml de Dowtherm-A are brought to reflux (about 235° C.) under a nitrogen atmosphere. 41 g (0.16 M) of 2-(4-fluorophenylamino)but-2-enedioic acid dimethyl ester are then introduced dropwise. The methanol formed is separated out. Refluxing is maintained for 10 minutes after the end of introduction. The reaction mixture is then cooled to about 50° C., followed by addition of 250 ml of petroleum ether: a solid precipitates out. It is filtered off by suction, washed three times with petroleum ether and then dried under reduced pressure.

27.4 g of a beige-coloured solid are obtained. A second crop is obtained by evaporating off, under reduced pressure, the petroleum ether and the residual methanol from the reaction medium, which is heated again to 240° C. for 30 minutes. After cooling and diluting with petroleum ether (2 volumes), the precipitate obtained is worked up as previously, to obtain 2.6 g of solid. The two crops are combined and washed with 400 ml of hot butanol. After filtration by suction and drying under reduced pressure: 26.3 g of solid.
Yield: 73%
m.p.: >250° C.
$^1$H NMR (DMSO-d$_6$):
12.2 (1H, s); 7.9 (1H, m); 7.7 (1H, m); 7.5 (1H, m); 3.85 (3H, s)

Methyl 4-ethoxy-6-fluoroquinoline-2-carboxylate 8.0 g (0.036 M) of methyl 6-fluoro-4-oxo-1,4-dihydroquinoline-2-carboxylate and 15.0 g (0.108 M) of potassium carbonate are introduced into 80 ml of DMF. The reaction mixture is stirred for 1 hour at 50° C. After addition of 3.0 ml (0.037 M) of iodoethane and heating for 12 hours at 50° C., the reaction medium is poured into 400 ml of demineralized water. A brown solid precipitates out. The solid is filtered off, washed thoroughly with water and then with isopropyl ether, and finally dried under vacuum at 40° C.

5.54 g of brown solid are obtained.
Yield: 61%
m.p.=149° C.
$^1$H NMR (DMSO-d$_6$):
8.35 (1H, m); 7.9 (2H, m); 7.7 (1H, m);
4.6 (2H, q); 4.2 (3H, s); 1.75 (3H, t)

4-Ethoxy-6-fluoroquinoline-2-carboxylic acid (1)

A suspension of 14.0 g (0.056 M) of methyl 4-ethoxy-6-fluoro-2-quinoline-carboxylate in 100 ml of a solution comprising 2.32 g (0.056 M) of sodium hydroxide (at 97%) in 100 ml of methanol and 100 ml of demineralized water is refluxed for 5 hours. The solution, which has become clear, is cooled and then acidified to pH=1 with 6N hydrochloric acid solution.

The reaction medium is then poured into 700 ml of an ice-water mixture. The precipitate formed is stirred for a further 1 hour, filtered off, washed with demineralized water until the filtrate is neutral, and then with isopropyl ether, and finally dried under vacuum.

11.66 g of white solid are obtained.
Yield: 88%
m.p.=207° C.
$^1$H NMR (DMSO-d$_6$):
8 (1H, m); 7.65 (2H, m); 7.42 (1H, s); 4.27 (2H, q); 1.39 (3H, t)

By way of example, the following compounds are prepared according to the procedure of Example 1:

(2): 4-(4-Bromo-2-fluorobenzyloxy)-6-fluoroquinoline-2-carboxylic acid m.p.=>250° C.
$^1$H NMR (DMSO-d$_6$):
8.5-7.7 (7H, m); 5.75 (2H, s);

(3): 4-(Benzothiazol-2-ylmethoxy)-6-fluoroquinoline-2-carboxylic acid m.p.=>250° C.
$^1$H NMR (DMSO-d$_6$):
8.15-7.3 (8H, m); 5.85 (2H, s);

(4): 4-(4-Bromo-2-fluorobenzyloxy)-6-methoxyquinoline-2-carboxylic acid, sodium salt m.p.=>250° C.
$^1$H NMR (DMSO-d$_6$):
$^2$8.3 (1H, m); 7.85-7.45 (6H, m); 5.55 (2H, s); 4 (3H, s)

(5): 4-({(E)-4-[(2-Carboxy-6-fluoro-4-quinolinyl)oxy]-2-butenyl}oxy)-6-fluoro-2-quinolinecarboxylic acid m.p.=>250° C.
$^1$H NMR (TFA):
9.07-8.57 (8H, m), 7.06 (2H, s); 6.11 (4H, s);

(6): 6-Fluoro-4-(3-methylbut-2-enyloxy)quinoline-2-carboxylic acid m.p.=>250° C.
$^1$H NMR (DMSO-d$_6$):
8.5 (1H, m) 7.86 (3H, m); 5.8 (1H, m); 5.08 (1H, s); 5.05 (1H, s); 2.02 (6H, s)

(7): 4-(2'-Cyanobiphenyl-4-ylmethoxy)-6-fluoroquinoline-2-carboxylic acid m.p.=>250° C.
$^1$H NMR (DMSO-d$_6$):
8.35 (1H, m); 7.99-7.34 (12H, m); 5.57 (2H, s)

4-Ethoxy-6-fluoroquinoline-2-carboxylic acid m.p.=205° C.
$^1$H NMR (DMSO-d$_6$):
8.01 (1H, m); 7.69-7.42 (3H, m); 4.27 (2H, q); 1.40 (3H, t)

EXAMPLE 2

4-Allyloxy-6-fluoroquinoline-2-carboxylic acid

-4-Allyloxy-6-fluoroquinoline-2-carboxylic acid methyl ester 374 mg (2.7 mM) of potassium carbonate and then a solution of 199.95 mg (0.904 mM) of methyl 6-fluoro-4-oxo-1,4-dihydroquinoline-2-carboxylate dissolved in 4 ml of hot dimethylformamide, are respectively added into a container. After heating at 50° C. with stirring for one hour, 109.36 (0.904 mM) of allyl bromide are added to the reaction medium. Stirring is continued for 4 hours at 50° C. and then for 8 hours at room temperature. The medium is diluted with 20 ml of demineralized water. A solid precipitates out with stirring. It is filtered off, washed with demineralized water and then dried.

4-Allyloxy-6-fluoroquinoline-2-carboxylic acid

The above ester is hydrolysed with one equivalent of normal caustic soda comprising an equal volume of methanol, for one hour at 60° C. The reaction medium is then taken up in 15 ml of demineralized water, washed twice with ethyl acetate, acidified with normal hydrochloric acid solution and then extracted twice with ethyl acetate. The organic phases are combined and then concentrated under reduced pressure.

The solid obtained is analysed.

By way of example, the following compounds are prepared according to the procedure of Example 2:

| Compound | Structure | Theoretical mass | Mass found |
|---|---|---|---|
| 8 | (6-fluoroquinoline-2-carboxylic acid methyl ester, 4-O-CH$_2$CN) | 260.2 | 260.1 |
| 9 | (6-fluoroquinoline-2-carboxylic acid methyl ester, 4-O-CH$_2$CH$_2$Cl) | 283.7 | 283.9 |
| 10 | (6-fluoroquinoline-2-carboxylic acid methyl ester, 4-O-CH$_2$C(O)NH$_2$) | 278.2 | 278.9 |
| 11 | (6-fluoroquinoline-2-carboxylic acid methyl ester, 4-O-CH$_2$CH=CH$_2$) | 261.3 | 261.9 |

| Compound | Structure | Theoretical mass | Mass found |
|---|---|---|---|
| 12 | 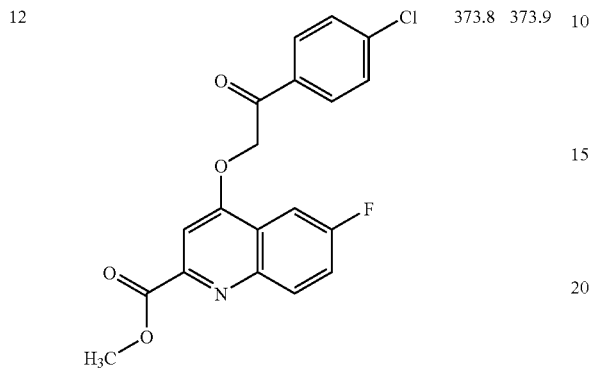 | 373.8 | 373.9 |
| 13 | 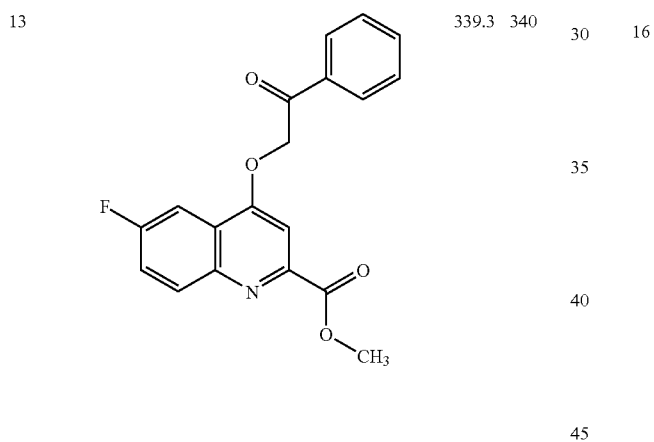 | 339.3 | 340 |
| 14 | 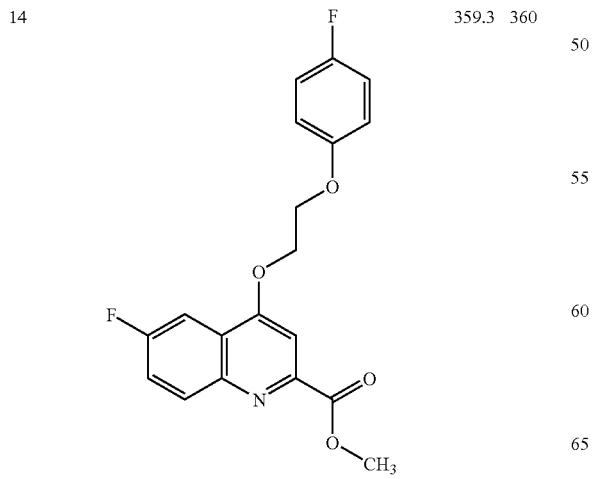 | 359.3 | 360 |
| Compound | Structure | Theoretical mass | Mass found |
|---|---|---|---|
| 15 | 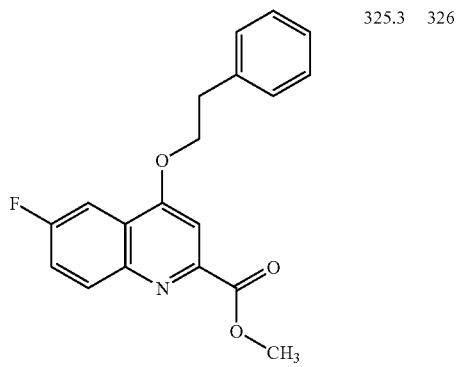 | 325.3 | 326 |
| 16 | 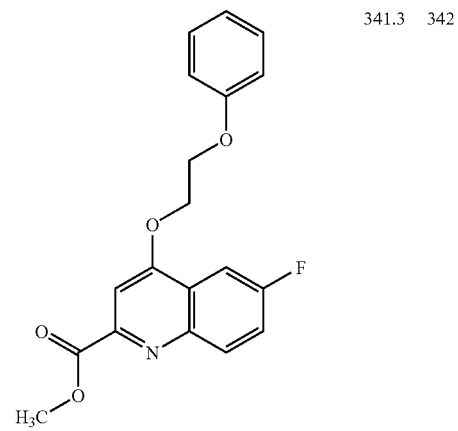 | 341.3 | 342 |
| 17 | 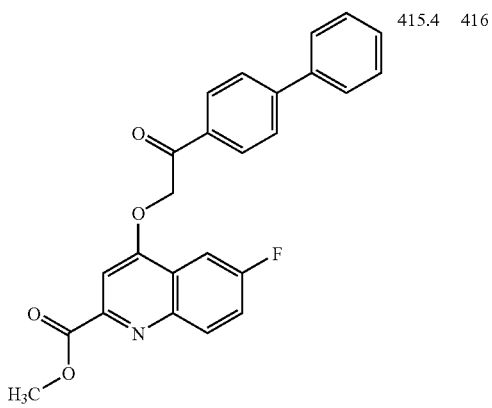 | 415.4 | 416 |

-continued

| Compound | Structure | Theoretical mass | Mass found |
|---|---|---|---|
| 18 | 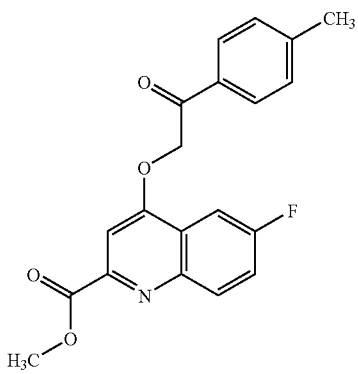 | 353.4 | 354 |
| 19 | 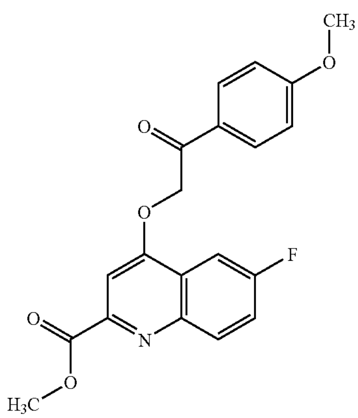 | 369.4 | 370 |
| 20 | 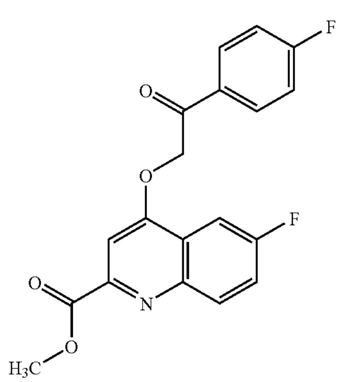 | 357.3 | 358 |
| 21 | | 408.2 | 407.9 |
| 22 | | 369.4 | 370 |
| 23 | | 403.8 | 404 |

-continued
| Compound | Structure | Theoretical mass | Mass found |
|---|---|---|---|
| 24 | 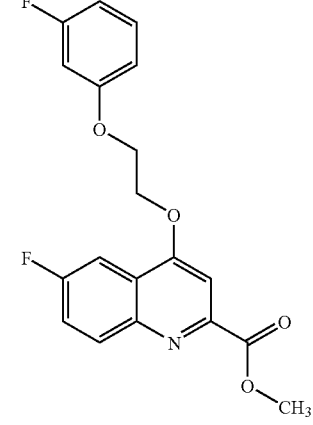 | 359.3 | 360 |
| 25 | 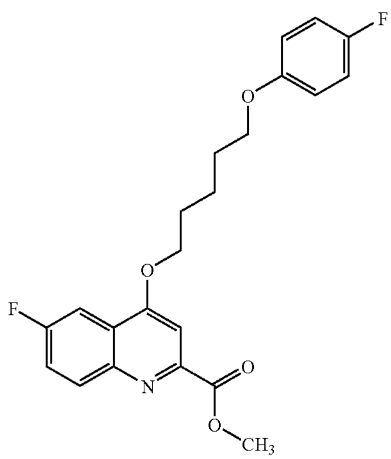 | 401.4 | 402 |
| 26 | 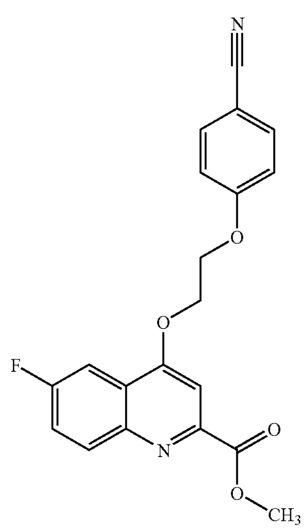 | 366.4 | 368 |
-continued
| Compound | Structure | Theoretical mass | Mass found |
|---|---|---|---|
| 27 | 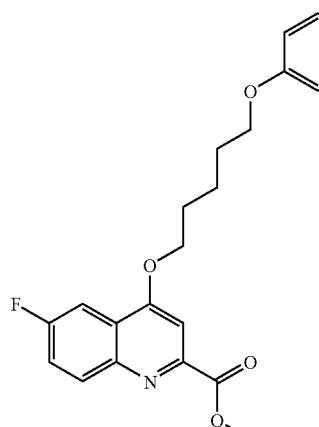 | 434.4 | 435 |
| 28 | 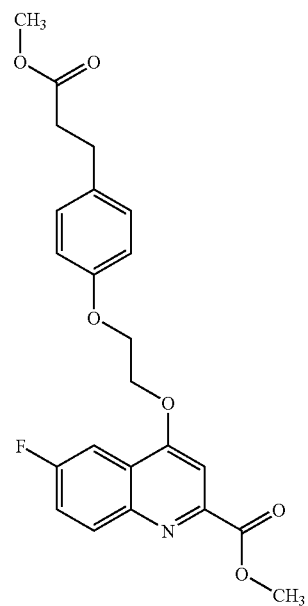 | 427.4 | 428 |
| 29 | 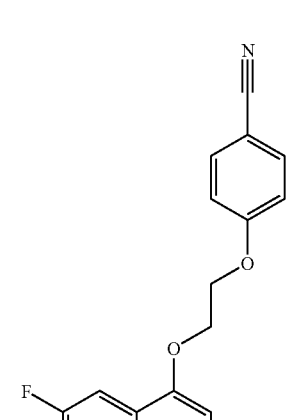 | 391.4 | 392 |

| Compound | Structure | Theoretical mass | Mass found |
|---|---|---|---|
| 30 | (structure) | 371.4 | 372 |
| 31 | (structure) | 445.5 | 446 |
| 32 | (structure) | 391.4 | 392 |
| 33 | (structure) | 394.4 | 395 |
| 34 | (structure) | 411.4 | 412 |
| 35 | (structure) | 369.4 | 370 |

| Compound | Structure | Theoretical mass | Mass found |
|---|---|---|---|
| 36 | | 411.4 | 412 |
| 37 | | 445.5 | 446 |
| 38 | | 399.4 | 400 |
| 39 | 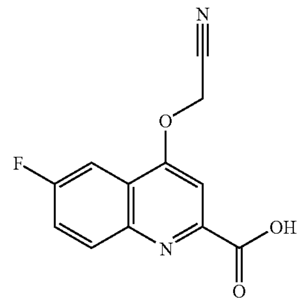 | 246.2 | 245 |
| 40 | 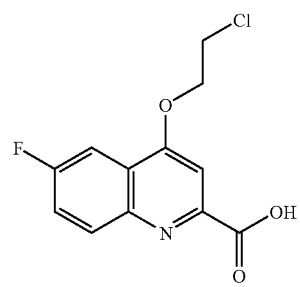 | 269.7 | 268 |
| 41 | 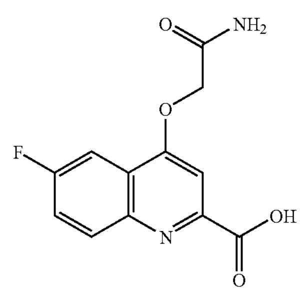 | 264.2 | 263 |
| 42 | 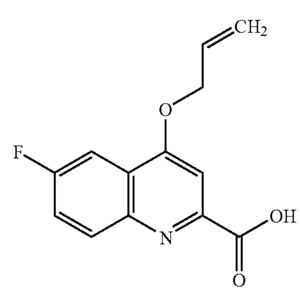 | 247.2 | 246.1 |

| Compound | Structure | Theoretical mass | Mass found |
|---|---|---|---|
| 43 | 6-fluoro-4-(3-chloropropoxy)quinoline-2-carboxylic acid | 283.7 | 282 |
| 44 | 6-fluoro-4-(3-chloro-2-methylpropoxy)quinoline-2-carboxylic acid | 297.7 | 296 |
| 45 | 6-fluoro-4-pentyloxyquinoline-2-carboxylic acid | 277.3 | |
| 46 | 6-fluoro-4-(cyclohexylmethoxy)quinoline-2-carboxylic acid | 303.3 | 302.1 |
| 47 | 6-fluoro-4-[2-(4-fluorophenoxy)ethoxy]quinoline-2-carboxylic acid | 345.3 | 344 |
| 48 | 6-fluoro-4-(2-phenylethoxy)quinoline-2-carboxylic acid | 311.3 | 310 |
| 49 | 6-fluoro-4-(3-phenylpropoxy)quinoline-2-carboxylic acid | 325.3 | 324 |

-continued

| Compound | Structure | Theoretical mass | Mass found |
|---|---|---|---|
| 50 | 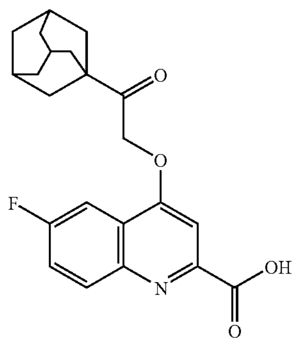 | 383.4 | 382.1 |
| 51 | 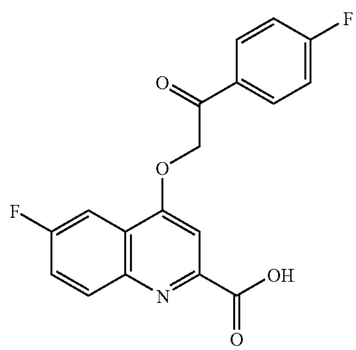 | 343.3 | 342 |
| 52 | 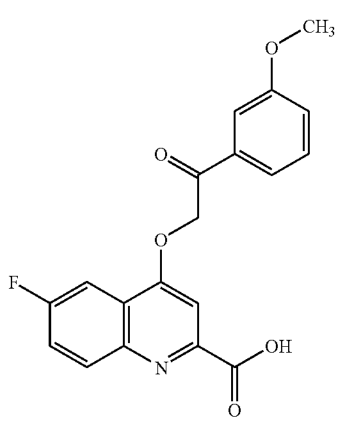 | 355.3 | 354 |

-continued

| Compound | Structure | Theoretical mass | Mass found |
|---|---|---|---|
| 53 | | 389.8 | 388 |
| 54 | | 345.3 | 344 |
| 55 | | 406.2 | 406 |

-continued

| Compound | Structure | Theoretical mass | Mass found |
|---|---|---|---|
| 56 | 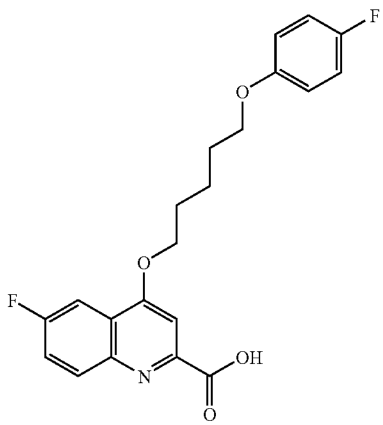 | 387.4 | 386 |
| 57 | 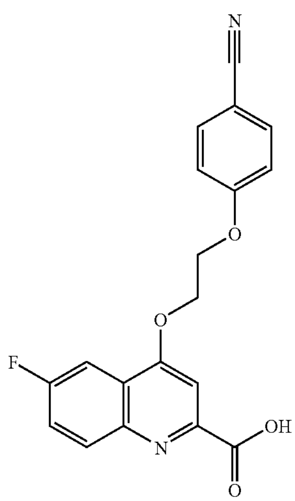 | 352.3 | 351 |
| 58 | 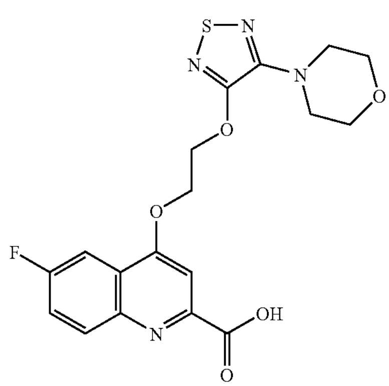 | 420.4 | 419.1 |

-continued

| Compound | Structure | Theoretical mass | Mass found |
|---|---|---|---|
| 59 | 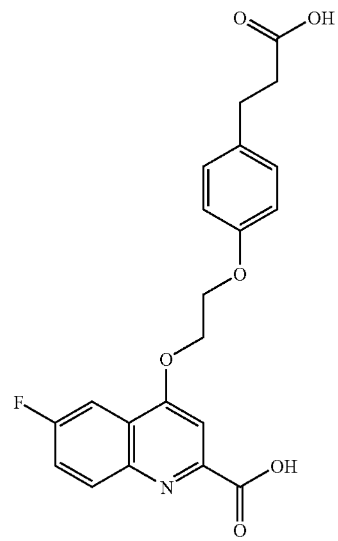 | 399.4 | 398 |
| 60 | 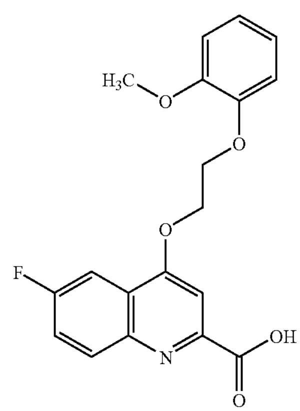 | 357.3 | 356 |
| 61 | 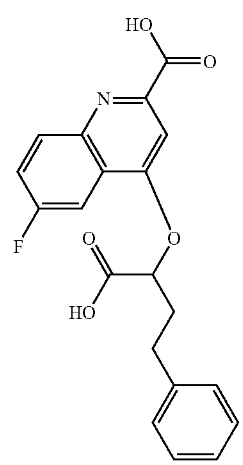 | 369.4 | 368 |

-continued

| Compound | Structure | Theoretical mass | Mass found |
|---|---|---|---|
| 62 | [6-fluoro-4-(2-(2,3-dimethylphenoxy)ethoxy)quinoline-2-carboxylic acid] | 355.4 | 354.1 |
| 63 | [6-fluoro-4-(2-(3,4-dimethoxyphenyl)-2-oxoethoxy)quinoline-2-carboxylic acid] | 385.4 | 384 |
| 64 | [methyl 4-(3-chloropropoxy)-6-fluoroquinoline-2-carboxylate] | 297.7 | |
| 65 | [methyl 4-(3-chloro-2-methylpropoxy)-6-fluoroquinoline-2-carboxylate] | 311.7 | |

-continued

| Compound | Structure | Theoretical mass | Mass found |
|---|---|---|---|
| 66 | [methyl 4-(pentan-3-yloxy)-6-fluoroquinoline-2-carboxylate] | 291.3 | |
| 67 | [methyl 4-(heptan-2-yloxy)-6-fluoroquinoline-2-carboxylate] | 319.4 | |
| 68 | [methyl 4-(2-(2,4-dimethoxyphenyl)-2-oxoethoxy)-6-fluoroquinoline-2-carboxylate] | 399.4 | |
| 69 | [methyl 4-(3,3-dimethyl-2-oxobutoxy)-6-fluoroquinoline-2-carboxylate] | 319.3 | |

| Compound | Structure | Theoretical mass | Mass found |
|---|---|---|---|
| 70 | (6-fluoro-4-(3-phenoxypropoxy)quinoline-2-carboxylic acid methyl ester) | 355.4 | |

Insulin Secretion Test

According to the method described in *Endocrinology*, 1992 vol. 130 (1) pp. 167-178

| COMPOUND | STRUCTURE | C | INS. SEC. |
|---|---|---|---|
| 1 | (6-fluoro-4-ethoxyquinoline-2-carboxylic acid) | $10^{-5}$ M | 172% |
| 63 | (structure with 3,4-dimethoxyphenyl ketone) | $10^{-5}$ M | 192% |
| 64 | (6-fluoro-4-(3-chloropropoxy)quinoline-2-carboxylic acid methyl ester) | $10^{-5}$ M | 179% |
| 65 | (6-fluoro-4-(3-chloro-2-methylpropoxy)quinoline-2-carboxylic acid methyl ester) | $10^{-5}$ M | 161% |

C corresponds to the concentration of test compound according to the invention INS. SEC. corresponds to the percentage of insulin secretion.

Study of the Antidiabetic Activity in N0STZ Rats

The antidiabetic activity of the compounds of the formula (I) via the oral route, on an experimental model of non-insulin-dependent diabetes induced in rats by means of steptozotocin, was determined as follows.

The model of non-insulin-dependent diabetes is obtained in the rats by means of a neonatal injection (on the day of birth) of steptozotocin.

The diabetic rats used are eight weeks old. The animals are housed, from the day of birth to the day of the experiment, in an animal house at a regulated temperature of 21 to 22° C. and subjected to a fixed cycle of light (from 7 a.m. to 7 p.m.) and darkness (from 7p.m. to 7 a.m.). Their food consisted of a maintenance diet, and water and food were given "ad libitum", with the exception of fasting two hours before the tests, during which period the food is removed (post-absorptive state).

The rats are treated orally for one (D1) or four (D4) days with the test product. Two hours after the final administration of the product and 30 minutes after anaesthetizing the animals with pentobarbital sodium (Nembutal®), a 300 µl blood sample is taken from the end of the tail.

By way of example, the results obtained are collated in the table below.

These results show the efficacy of the compounds mentioned in reducing glycaemia in the case of diabetic animals. These results are expressed as a percentage change in the glycaemia on D4 (number of days of treatment) relative to D0 (before the treatment).

| IN-VIVO TEST (N0 STZ RAT) | | |
|---|---|---|
| REFERENCE | STRUCTURE | Percentage decrease in glycaemia at 200 mg/kg |
| 1 | | −27 |
| 5 | | −17 |
| 6 | | −10 |

The invention claimed is:

1. A compound, which is
4-ethoxy-6-fluoroquinoline-2-carboxylic acid;
4-({(E)-4-[(2-carboxy-6-fluoro-4-quinolinyl)oxy]-2-butenyl}oxy)-6-fluoroquinoline-2-carboxylic acid;
6-fluoro-4-(3-methylbut-2-enyloxy)quinoline-2-carboxylic acid;
4-[2-(3,4-dimethoxyphenyl)-2-oxo-ethoxy]-6-fluoroquinoline-2-carboxylic acid;
methyl 4-(3-chloropropoxy)-6-fluoroquinoline-2-carboxylate;
methyl 4-(3-chloro-2-methylpropoxy)-6-fluoroquinoline-2-carboxylate;
a pharmaceutically acceptable salt thereof, or
a tautomeric form, enantiomer, diastereoisomer or epimer thereof.

2. A compound according to claim 1, which is
4-ethoxy-6-fluoroquinoline-2-carboxylic acid;
4-({(E)-4-[(2-carboxy-6-fluoro-4-quinolinyl)oxy]-2-butenyl}oxy)-6-fluoroquinoline-2-carboxylic acid;
6-fluoro-4-(3-methylbut-2-enyloxy)quinoline-2-carboxylic acid;
4-[2-(3,4-dimethoxyphenyl)-2-oxo-ethoxy]-6-fluoroquinoline-2-carboxylic acid;
methyl 4-(3-chloropropoxy)-6-fluoroquinoline-2-carboxylate;
methyl 4-(3-chloro-2-methylpropoxy)-6-fluoroquinoline-2-carboxylate; or
a pharmaceutically acceptable salt thereof.

3. A pharmaceutical composition, comprising a compound of claim 1 and a pharmaceutically acceptable carrier.

4. A pharmaceutical composition, comprising a compound of claim 2 and a pharmaceutically acceptable carrier.

5. A method for treating a hyperglycaemia-related pathology, which is diabetes, type II diabetes, dyslipidaemia, obesity, arterial hypertension, atherosclerosis, microangiopathy, macroangiopathy, retinopathy, neuropathy or hyperglycaemia, comprising administering to a patient in need thereof an effective amount of a pharmaceutical composition according to claim 3.

6. A method according to claim 5, which is for treating diabetes.

7. A method for treating a hyperglycaemia-related pathology, which is diabetes, type II diabetes, dyslipidaemia, obesity, arterial hypertension, atherosclerosis, microangiopathy, macroangiopathy, retinopathy, neuropathy or hyperglycaemia, comprising administering to a patient in need thereof an effective amount of a pharmaceutical composition according to claim 4.

8. A method according to claim 7, which is for treating diabetes, type II diabetes or hyperglycaemia.

9. A compound according to claim 1, which is 4-ethoxy-6-fluoroquinoline-2-carboxylic acid;
a pharmaceutically acceptable salt thereof, or
a tautomeric form, enantiomer, diastereoisomer or epimer thereof.

10. A compound according to claim 1, which is 4-({(E)-4-[(2-carboxy-6-fluoro-4-quinolinyl)oxy]-2-butenyl}oxy)-6-fluoroquinoline-2-carboxylic acid;
a pharmaceutically acceptable salt thereof, or
a tautomeric form, enantiomer, diastereoisomer or epimer thereof.

11. A compound according to claim 1, which is 6-fluoro-4-(3-methylbut-2-enyloxy)quinoline-2-carboxylic acid;
a pharmaceutically acceptable salt thereof, or
a tautomeric form, enantiomer, diastereoisomer or epimer thereof.

12. A compound according to claim 1, which is 4-[2-(3,4-dimethoxyphenyl)-2-oxo-ethoxy]-6-fluoroquinoline-2-carboxylic acid;
a pharmaceutically acceptable salt thereof, or
a tautomeric form, enantiomer, diastereoisomer or epimer thereof.

13. A compound according to claim 1, which is methyl 4-(3-chloropropoxy)-6-fluoroquinoline-2-carboxylate;
a pharmaceutically acceptable salt thereof, or
a tautomeric form, enantiomer, diastereoisomer or epimer thereof.

14. A compound according to claim 1, which is methyl 4-(3-chloro-2-methylpropoxy)-6-fluoroquinoline-2-carboxylate,
a pharmaceutically acceptable salt thereof, or
a tautomeric form, enantiomer, diastereoisomer or epimer thereof.

15. A method according to claim 5, which is for treating type II diabetes.

16. A method according to claim 5, which is for treating hyperglycaemia.

17. A method according to claim 5, which is for treating obesity.

18. A method according to claim 5, which is for treating arterial hypertension.

19. A method according to claim 5, which is for treating atherosclerosis.

20. A method according to claim 5, which is for treating dyslipidaemia, microangiopathy, macroangiopathy, retinopathy or neuropathy.

* * * * *